US00PP12591P2

(12) United States Plant Patent
Gross

(10) Patent No.: US PP12,591 P2
(45) Date of Patent: Apr. 30, 2002

(54) POINSETTIA PLANT NAMED 'ROMANCE'

(75) Inventor: Eduard Gross, Blanzac (FR)

(73) Assignee: Paul Ecke Ranch, Encinitas, CA (US)

( * ) Notice: Subject to any disclaimer, the term of this patent is extended or adjusted under 35 U.S.C. 154(b) by 0 days.

(21) Appl. No.: 09/563,935

(22) Filed: May 4, 2000

(51) Int. Cl.[7] ..... A01H 5/00
(52) U.S. Cl. ..... Plt./307

(58) Field of Search ..... Plt./307

*Primary Examiner*—Bruce R. Campell
*Assistant Examiner*—Anne Marie Grünberg
(74) *Attorney, Agent, or Firm*—C. A. Whealy

(57) ABSTRACT

A new and distinct cultivar of Poinsettia plant named 'Romance', characterized by its bright red flower bracts; very dark green leaves; compact, uniform, upright and somewhat spreading plant habit; freely branching habit; and good post-production longevity.

2 Drawing Sheets

BACKGROUND OF THE INVENTION

The present Invention relates to a new and distinct cultivar of Poinsettia plant, botanically known as *Euphorbia pulcherrima* Willd., and hereinafter referred to by the name 'Romance'.

The new Poinsettia is a naturally-occurring whole plant mutation of the *Euphorbia pulcherrima* Willd. cultivar 490, disclosed in U.S. Plant Pat. No. 7,825. The new Poinsettia was discovered and selected by the Inventor in a controlled environment in Blanzac, France. Compared to plants of the parent cultivar, plants of the new Poinsettia are more upright and can be grown closer together.

Asexual reproduction of the new Poinsettia by terminal cuttings taken at Encinitas, Calif., has shown that the unique features of this new Poinsettia are stable and reproduced true to type in successive generations of asexual reproduction.

BRIEF SUMMARY OF THE INVENTION

The following traits have been repeatedly observed and are determined to be the unique characteristics of 'Romance'. These characteristics in combination distinguish 'Romance' as a new and distinct cultivar:

1. Bright red-colored flower bracts.
2. Very dark green leaves.
3. Compact, uniform, upright and somewhat spreading plant habit.
4. Freely branching habit.
5. Good post-production longevity.

Plants of the new Poinsettia can be compared to plants of the Poinsettia cultivar Fiscor, disclosed in U.S. Plant Pat. No. 9,364. In side-by-side comparisons conducted in Encinitas, Calif., plants of the new Poinsettia differed from plants of the cultivar Fiscor in the following characteristics:

1. Plants of the new Poinsettia are more upright and more uniform in plant habit than plants of the cultivar Fiscor.
2. Plants of the new Poinsettia have smaller leaves and shorter petioles than plants of the cultivar Fiscor.
3. Plants of the new Poinsettia have smaller flower bracts and shorter bract petioles than plants of the cultivar Fiscor.
4. Plants of the new Poinsettia have smaller inflorescences and tighter cyathia clusters than plants of the cultivar Fiscor.

5. Flower bract color of the new Poinsettia does not fade whereas flower bract color of the cultivar Fiscor fades with development.

BRIEF DESCRIPTION OF THE PHOTOGRAPHS

The accompanying colored photographs illustrate the overall appearance of the new Poinsettia, showing the colors as true as it is reasonably possible to obtain in colored reproductions of this type. Colors in the photographs may differ slightly from the color values cited in the detailed botanical description which accurately describe the actual color of the new Poinsettia.

The photograph at the top of the first sheet comprises a side perspective view of a typical plant of 'Romance'.

The photograph at the bottom of the first sheet comprises a top perspective view of a typical plant of 'Romance'.

The photograph on the second sheet is a close-up view of typical bracts and leaves of 'Romance' (top) and 'Fiscor' (bottom).

DETAILED BOTANICAL DESCRIPTION

The new Poinsettia has not been observed under all possible environmental conditions. The phenotype may vary somewhat with variations in environment such as temperature, daylength and light intensity, without, however, any variance in genotype. The following observations and measurements describe plants grown in Encinitas, Calif., under commercial practice in a glass-covered greenhouse with day temperatures about 24° C., night temperatures about 19° C., and light levels about 4,000 foot-candles. Plants were grown in 16.5-cm pots, pinched one time, and flowered under naturally lengthening nights during the fall.

In the following description, color references are made to The Royal Horticultural Society Colour Chart except where general terms of ordinary dictionary significance are used.

Botanical classification: *Euphorbia pulcherrima* Willd. cultivar Romance.

Parentage: Naturally-occurring whole plant mutation of *Euphorbia pulcherrima* Willd. cultivar 490, disclosed in U.S. Plant Pat. No. 7,825.

Propagation:

*Type cutting.*—Terminal cuttings.

*Time to initiate roots.*—Summer: About 7 days at 24° C. Winter: About 10 days at 22° C.

*Time to develop roots.*—Summer: About 26 days at 24° C. Winter: About 26 days at 22° C.

*Rooting habit.*—Thick, freely branching.

Plant description:

*Plant form.*—Inverted triangle, top of plant rounded; mounding.

*Growth habit.*—Compact, upright and somewhat spreading. Very uniform. Freely branching. Branching is enhanced by removing the shoot apex. Moderately vigorous.

*Plant height.*—About 27.5 cm.

*Crop time.*–From unrooted cuttings to a flowering plant in a 16.5-cm container, about 18 weeks are required.

*Stem description.*—Number of lateral branches: About 7 lateral branches develop after removal of the terminal apex. Lateral branch length: About 20 cm. Internode length: About 1.75 cm. Stem color: 146A.

*Foliage description.*—Quantity of leaves per lateral branch: About 8. Length: About 11 cm. Width: About 9.5 cm. Shape: Mostly ovate with lobing. Apex: Acuminate. Base: Acute. Margin: Entire. Texture: Smooth; slight pubescence on lower surface. Color: Young foliage, upper surface: 147A. Young foliage, lower surface: 147B. Mature foliage, upper surface: Very dark green, darker than 147A. Mature foliage, lower surface: 147A. Venation, upper surface: 179B. Venation, lower surface: Midvein, 179A; laterals, 179B to 179C. Petiole: Length: About 4.75 cm. Diameter: About 2 mm. Color: 59A.

Inflorescence description:

*Inflorescence type and habit.*—Inflorescences are compound corymbs of cyathia with colored flower bracts subtending the cyathia.

*Natural flowering season.*—Autumn/winter in Northern Hemisphere. Flower initiation and development can be induced under long night conditions. Early flowering, response time is about 9.5 weeks.

*Quantity of inflorescences.*—One per lateral branch, usually about 7 per plant.

*Inflorescence size.*—Diameter: About 30 cm. Height (depth): About 6 cm.

*Flower bracts.*—Quantity of flower bracts per inflorescence: Usually about 12 primary bracts and about 6 smaller secondary bracts per inflorescence. Length, largest bracts: About 13.5 cm. Width, largest bracts: About 10 cm. Shape: Mostly ovate; occasionally lobed. Apex: Acuminate. Base: Acute. Margin: Entire. Texture: Smooth. Aspect: Mostly flat. Color: Developing, upper surface: 46A. Developing, lower surface: 46A to 46B. Mature, upper surface: 45A; color does not fade with subsequent development. Mature, lower surface: 45B to 45C. Bract petioles: Length: About 3.8 cm. Orientation: Horizontal to slightly drooping. Color: 59A.

*Cyathia.*—Quantity: Usually about 7 per corymb. Diameter of cyathia cluster: About 1.5 by 2 cm. Length: About 1 cm. Width: About 6 mm. Color: Immature: 144A. Mature: 144A to 144B.

*Peduncle.*—Length: About 4 mm. Aspect: Strong, erect. Color: 144B.

*Reproductive organs.*—Stamens: Stamen number: Typically more than 10 fertile stamens and numerous stamenodes per cyathium. Anther shape: Oblong. Anther length: About 1 mm. Anther color: 47B. Amount of pollen: Scarce. Pollen color: 9A. Pistils: None observed. Nectary color: 17A.

Disease resistance: Resistance to pathogens common to Poinsettias has not been observed on plants grown under commercial conditions.

Post-production longevity: Generally plants maintain good substance and bract color for about four weeks under interior conditions.

It is claimed:

1. A new and distinct cultivar of Poinsettia plant named 'Romance', as illustrated and described.

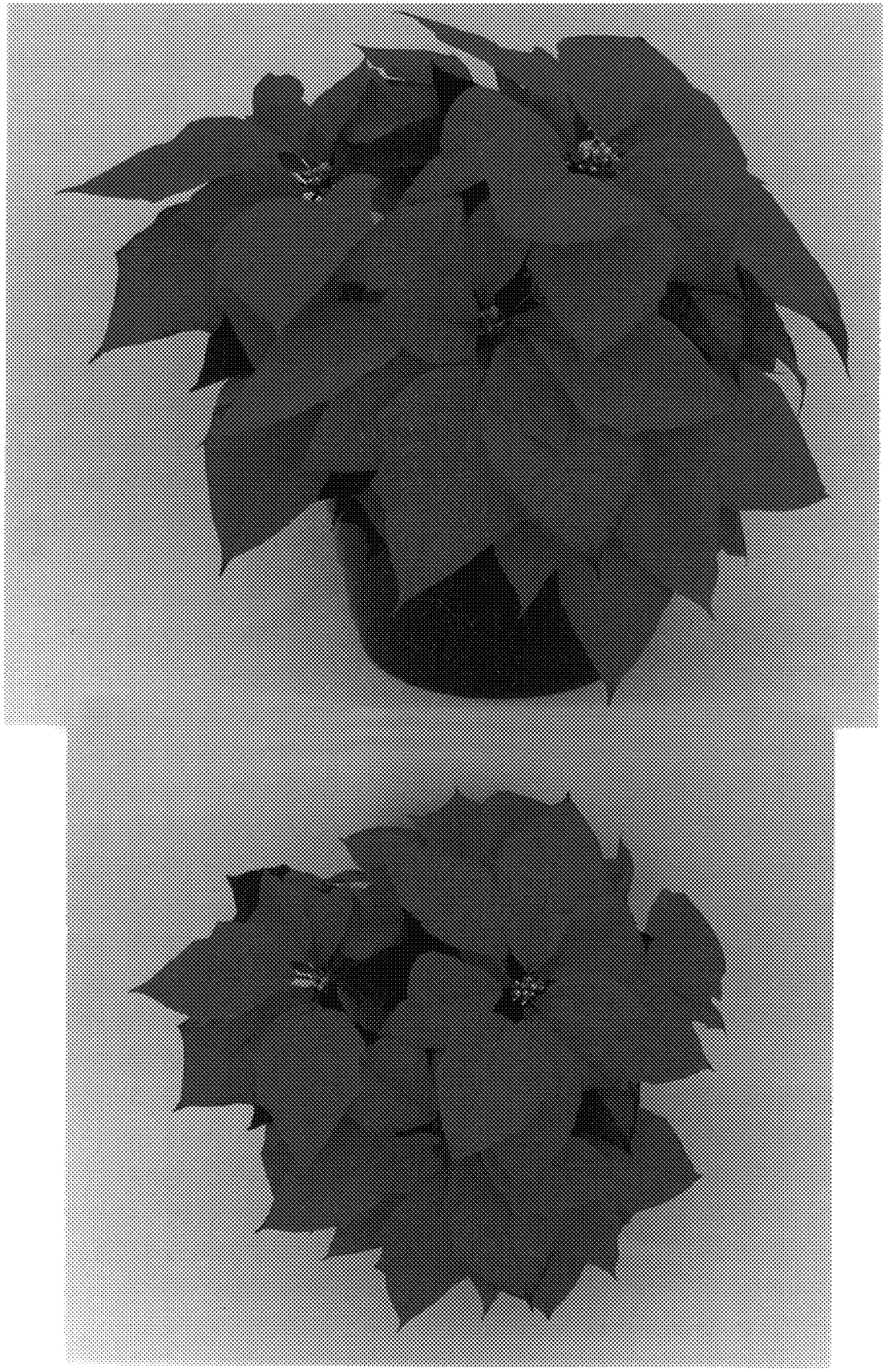

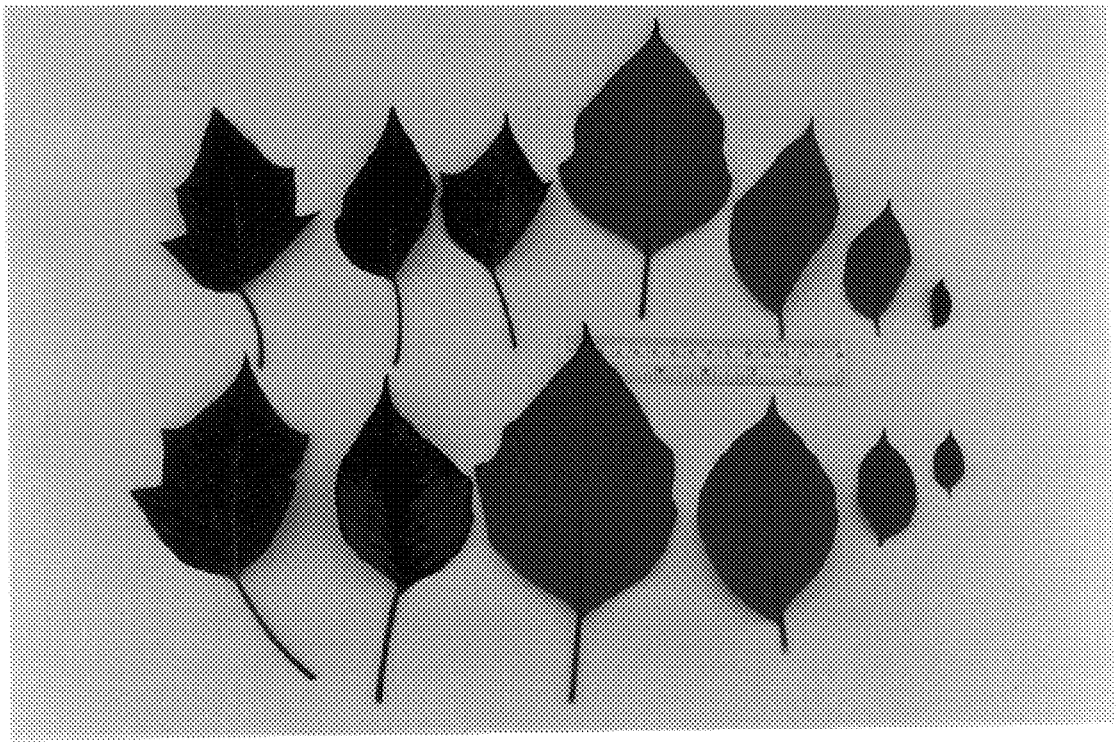

* * * * *